United States Patent
Koshimizu et al.

(10) Patent No.: US 10,024,774 B2
(45) Date of Patent: Jul. 17, 2018

(54) HARDNESS TEST APPARATUS AND HARDNESS TESTING METHOD

(71) Applicant: MITUTOYO CORPORATION, Kanagawa (JP)

(72) Inventors: Fumihiko Koshimizu, Zama (JP); Makoto Kaieda, Miyazaki (JP); Akira Takada, Yokohama (JP)

(73) Assignee: MITUTOYO CORPORATION, Kanagawa (JP)

( * ) Notice: Subject to any disclaimer, the term of this patent is extended or adjusted under 35 U.S.C. 154(b) by 104 days.

(21) Appl. No.: 15/255,782

(22) Filed: Sep. 2, 2016

(65) Prior Publication Data
US 2017/0074765 A1    Mar. 16, 2017

(30) Foreign Application Priority Data
Sep. 10, 2015   (JP) .................. 2015-178173

(51) Int. Cl.
*G01N 3/42*    (2006.01)

(52) U.S. Cl.
CPC ......... *G01N 3/42* (2013.01); *G01N 2203/008* (2013.01); *G01N 2203/0082* (2013.01);
(Continued)

(58) Field of Classification Search
CPC .......... G06T 2207/30164; G06T 7/001; G06T 7/0004; G06T 1/0007; G06K 2009/6213;
(Continued)

(56) References Cited

U.S. PATENT DOCUMENTS 8,566,735 B2   10/2013   Takemura et al.
8,849,588 B2    9/2014   Sawa et al.
(Continued)

FOREIGN PATENT DOCUMENTS

JP   2003-166923 A   6/2003
JP    2012-78306 A   4/2012

OTHER PUBLICATIONS

U.S. Appl. No. 15/251,295 to Takeshi Sawa et al., filed Aug. 30, 2016.
(Continued)

*Primary Examiner* — Jingge Wu
(74) *Attorney, Agent, or Firm* — Greenblum & Bernstein, P.L.C.

(57) ABSTRACT

A hardness tester includes a memory storing, as a parts program, definitions of measurement conditions including a coordinate system and test position defined with respect to an image of a standard reference sample; a pattern searcher performing a pattern searching process, with reference to a plurality of samples to be measured, using a pattern image based on the image of the standard reference sample, and detecting a number of samples having a shape identical to that of the standard reference sample, as well as a position and angle of the samples having the identical shape; a pattern definer defining a coordinate system and test position for each of the samples having the identical shape based on the position and angle of each of the samples having the identical shape; and a measurer measuring the hardness of the samples for which the coordinate system and test position have been defined.

8 Claims, 10 Drawing Sheets

(52) U.S. Cl.
CPC ........... *G01N 2203/0098* (2013.01); *G01N 2203/0647* (2013.01); *G01N 2203/0682* (2013.01)

(58) Field of Classification Search
CPC ............. G06K 2209/19; G06K 9/6201; G06K 9/6215; G01N 3/42
See application file for complete search history.

(56) References Cited

U.S. PATENT DOCUMENTS

| | | | | |
|---|---|---|---|---|
| 2004/0096093 | A1* | 5/2004 | Hauck | G01N 3/08 382/141 |
| 2004/0134263 | A1* | 7/2004 | Tsujii | G01N 3/42 73/81 |
| 2012/0087567 | A1* | 4/2012 | Takemura | G01N 3/42 382/141 |
| 2013/0215263 | A1* | 8/2013 | Ariga | G06T 3/4038 348/135 |
| 2013/0258094 | A1* | 10/2013 | Takemura | G01N 3/068 348/92 |
| 2014/0177937 | A1* | 6/2014 | Ariga | G01N 3/068 382/141 |
| 2015/0287177 | A1* | 10/2015 | Kaieda | G06K 9/3216 348/142 |
| 2016/0093068 | A1 | 3/2016 | Sugai et al. | |

OTHER PUBLICATIONS

U.S. Appl. No. 15/255,753 to Eiji Furuta et al., filed Sep. 2, 2016.
U.S. Appl. No. 15/251,324 to Takeshi Sawa et al., filed Aug. 30, 2016.

* cited by examiner

-- PRIOR ART --

-- PRIOR ART --

HARDNESS TEST APPARATUS AND HARDNESS TESTING METHOD

CROSS-REFERENCE TO RELATED APPLICATIONS

The present application claims priority under 35 U.S.C. § 119 of Japanese Application No. 2015-178173, filed on Sep. 10, 2015, the disclosure of which is expressly incorporated by reference herein in its entirety.

BACKGROUND OF THE INVENTION

1. Field of the Invention

The present invention relates to a hardness tester and to a hardness testing method.

2. Description of Related Art

A conventional hardness tester is known which measures hardness of a sample based on dimensions of an indentation formed by pressing an indenter against the sample (work piece) with a predetermined test force. For example, a Vickers hardness tester measures a length of diagonal lines of an indentation formed by pressing a quadrangular pyramidal indenter into a surface of the sample, and calculates hardness based on the measured length of the diagonal lines of the indentation (see, for example, Japanese Patent Laid-open Publication No. 2012-78306).

In recent years, in cases where a plurality of samples having an identical shape are repeatedly measured using the above hardness tester, a "parts manager" has been used. A parts manager is a function used when repeatedly executing a program of a test pattern laid out for one sample (a parts program) on another sample having an identical shape. For example, a parts manager settings screen G2 shown in FIG. 10 includes a parts count definer 201 defining a number of samples having an identical shape arranged in each of a column direction and a row direction; and an interval definer 202 defining an interval between samples adjacent in the column direction and an interval between samples adjacent in the row direction. By defining the number of samples present in each of the column and row directions as well as the intervals between adjacent samples in the column and row directions on the parts manager settings screen G2, an identical test pattern can be defined for a plurality of samples. As shown in FIG. 11, in a case where the orientations and intervals, for example, of the samples S are regular, defining a test pattern for the plurality of samples can be facilitated by using the parts manager.

However, in a case where the orientations and intervals of the samples are not regular, the test pattern cannot be easily defined with the parts manager settings screen G2 shown in FIG. 10. Instead, after defining the test pattern, an extensive recovery process is required of a user, such as correcting the position and direction of each sample. Even when the orientations and intervals of the samples are made regular using a jig, for example, a sample may slip out of arrangement, or the number of samples may differ at the time the parts program is recorded and the time the parts program is executed. In such cases, when the parts program is executed according to the number of samples defined at the time the parts program is recorded, a measurement error may occur at measurement locations where no sample is present. Accordingly, a separate operation is required to instruct that a measurement be omitted, negatively affecting operability.

SUMMARY OF THE INVENTION

The present invention provides a hardness tester and a hardness testing method capable of improving operability when repeatedly measuring hardness of a plurality of samples having an identical shape.

One aspect of the present invention to address the above is a hardness tester measuring hardness of a sample by loading a predetermined test force on the sample with an indenter to form an indentation in a surface of the sample, then performing one of a measurement of dimensions of the indentation and a measurement of a pressing depth of the indenter when forming the indentation. The hardness tester includes: a memory storing, as a parts program, definitions of measurement conditions including a coordinate system and test position, which are defined with respect to an image of a standard reference sample to be used as a standard reference when performing repeated measurements of the hardness of samples having identical shapes; a pattern searcher performing a pattern searching process, with reference to a plurality of samples to be measured, using a pattern image based on the image of the standard reference sample, and detecting a number of samples having a shape identical to that of the standard reference sample, as well as a position and angle of each of the samples having the identical shape; a pattern definer defining a coordinate system and test position for each of the samples having the identical shape, based on the position and angle of each of the samples having the identical shape detected by the pattern searcher, and on the parts program stored in the memory; and a measurer executing hardness testing with respect to the samples for which the coordinate system and test position have been defined by the pattern definer, and measuring the hardness of the samples.

In another aspect of the present invention, after the hardness of one sample is measured by the measurer, the pattern definer defines the coordinate system and test position for the next sample to be measured from among the samples having the identical shape.

In another aspect of the present invention, the hardness tester includes a sample count definer defining the number of samples having the identical shape detected by the pattern searcher as a number of repetitions, which is the number of samples for which the same test pattern is repeated.

In another aspect of the present invention, the hardness tester includes a calculator calculating the shortest test route when executing a single hardness test for all of the samples having the identical shape, based on the test position defined by the pattern definer for each sample having the identical shape. The measurer executes hardness testing based on the test route calculated by the calculator.

Another aspect of the present invention is a hardness testing method of a hardness tester measuring hardness of a sample by loading a predetermined test force on the sample with an indenter to form an indentation in a surface of the sample, then performing one of a measurement of dimensions of the indentation and a measurement of a pressing depth of the indenter when forming the indentation. The hardness testing method includes: performing a pattern searching process with reference to a plurality of samples to be measured, the pattern searching process being performed using a pattern image based on an image of a standard reference sample to be used as a standard reference when performing repeated measurements of the hardness of samples having identical shapes, and detecting a number of samples having a shape identical to that of the standard reference sample, as well as a position and angle of each of the samples having the identical shape; pattern definition defining a coordinate system and test position for each of the samples having the identical shape based on the position and angle of each of the samples having the identical shape detected in the pattern searching, and on a parts program defining measurement conditions, including a coordinate system and test position, with respect to an image of the standard reference sample; and measuring the hardness of the samples for which the coordinate system and test position have been defined in the pattern definition.

According to the present invention, operability when repeatedly measuring hardness of a plurality of samples having an identical shape can be improved.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the forms of the present invention may be embodied in practice.

Figure 1:
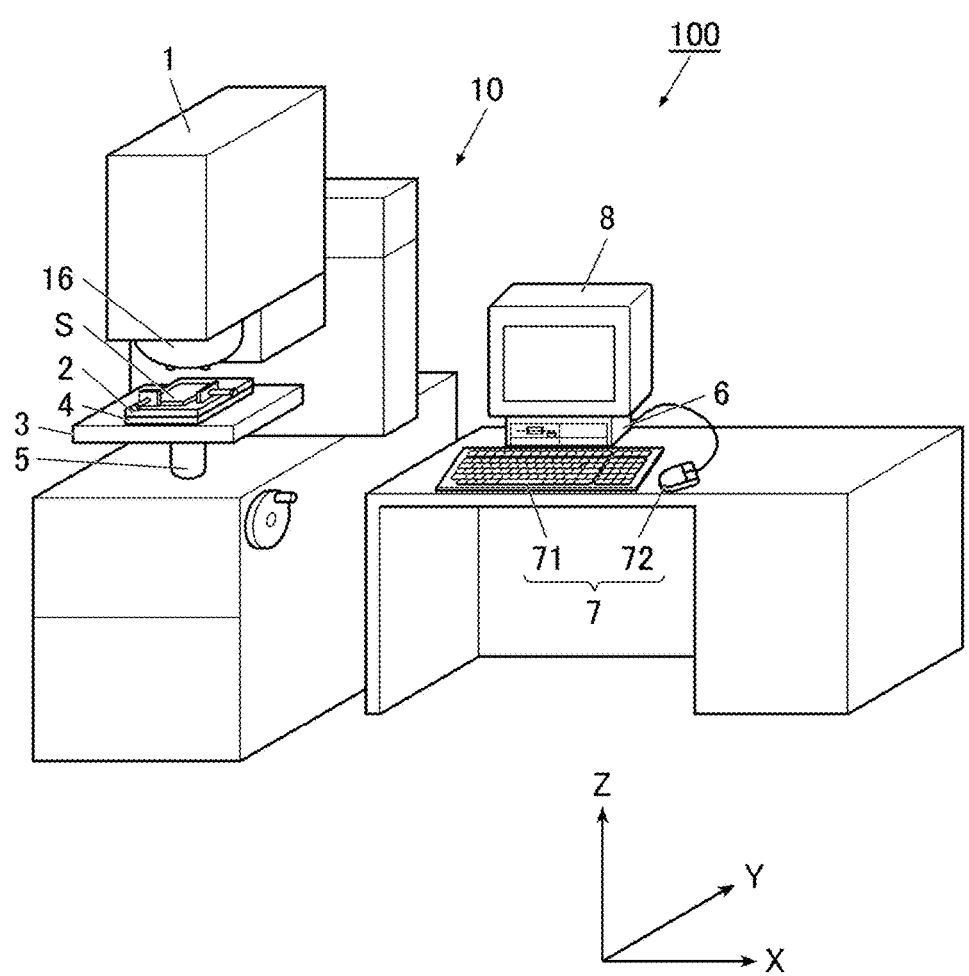
FIG. 1 is a perspective view illustrating an overall configuration of a hardness tester according to the present invention.

An embodiment of the present invention is described in detail below with reference to the drawings. Moreover, in the following description, an X direction is a left-right direction, a Y direction is a front-back direction, and a Z direction is an up-down direction in FIG. 1. In addition, an X-Y plane is a horizontal plane.

A hardness tester 100 is a Vickers hardness tester, for example, that includes an indenter 14a (see FIG. 3) having a square planar shape. As shown in FIGS. 1 to 4, the hardness tester 100 is configured to include a tester main body 10, a controller 6, a console 7, and a monitor 8.

Figure 2:
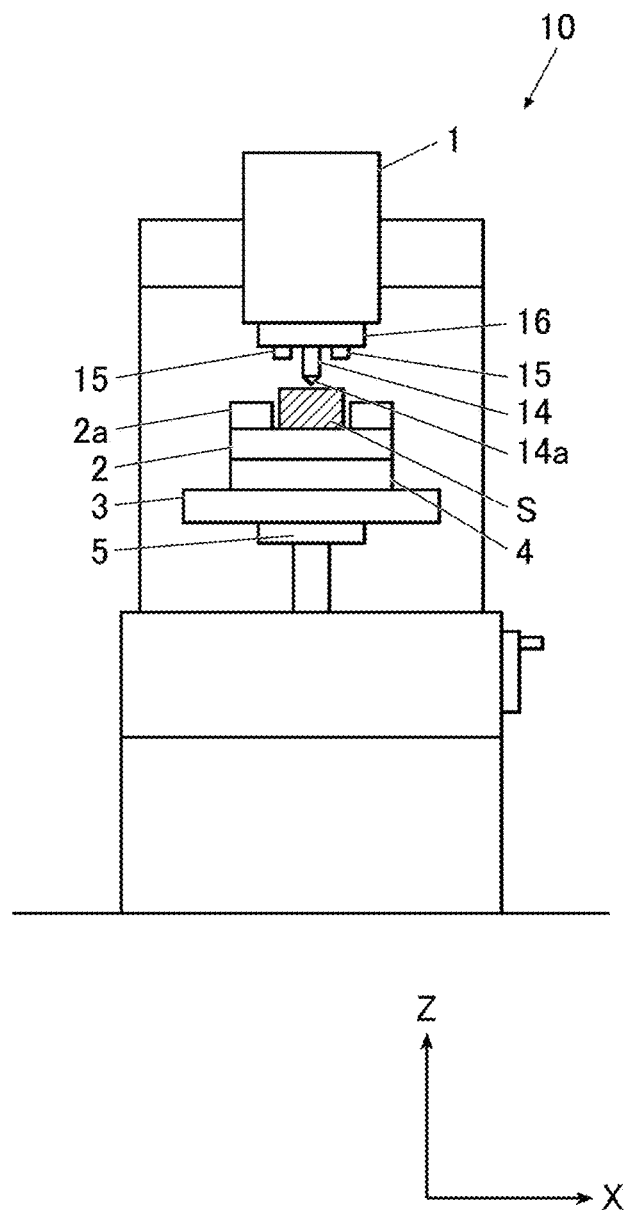
FIG. 2 is a schematic view illustrating a tester main body of the hardness tester according to the present invention.

As shown in FIG. 2, the tester main body 10 includes a hardness measurer 1 measuring hardness of a sample S; a sample stage 2 on which the sample S is placed; an XY stage 3 displacing the sample stage 2; an AF stage 4 enabling focusing on a surface of the sample S; and an elevator mechanism 5 raising and lowering the sample stage 2 (the XY stage 3 and the AF stage 4).

Figure 3:
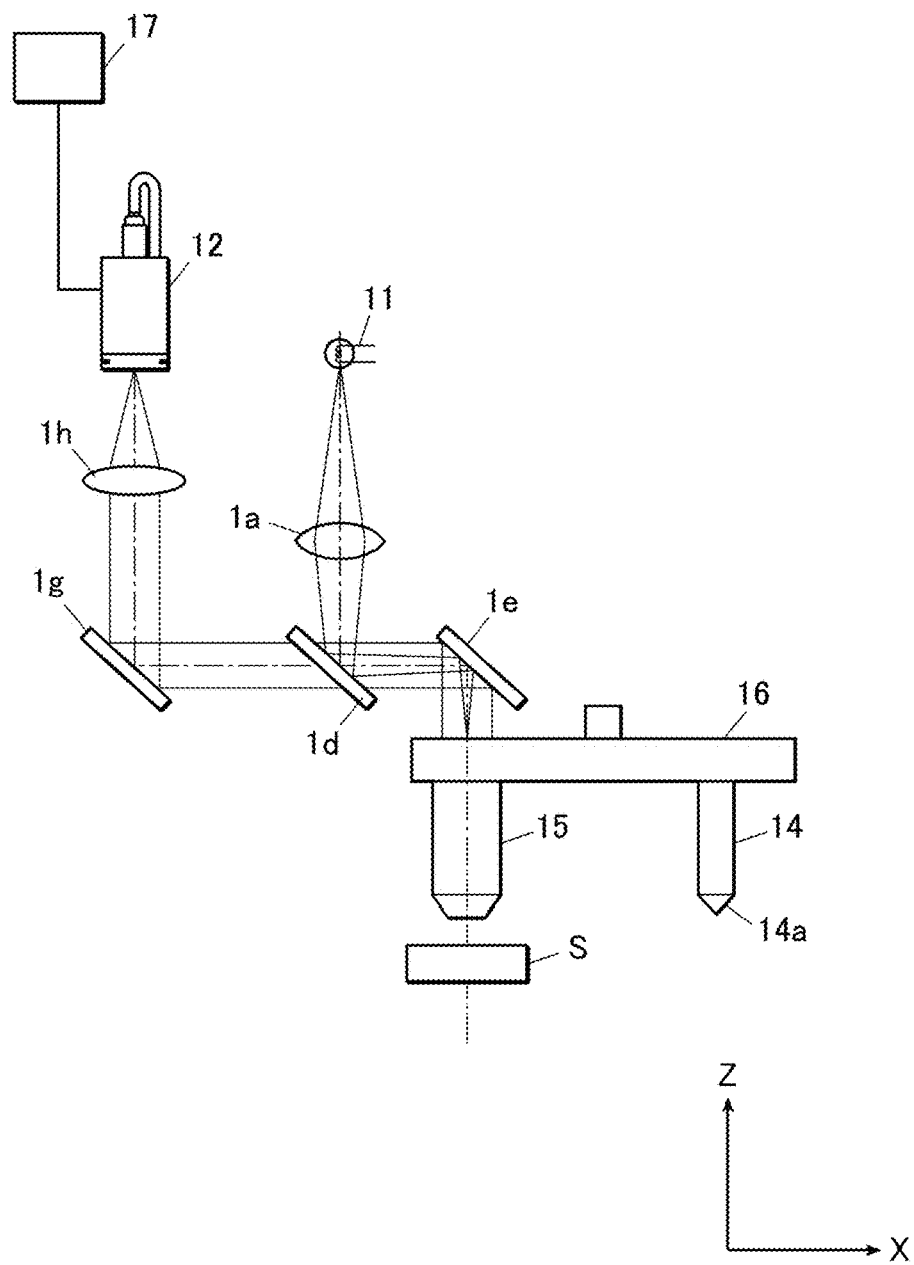
FIG. 3 is a schematic view illustrating a hardness measurer of the hardness tester according to the present invention.

As shown in FIG. 3, the hardness measurer 1 is configured with an illuminating device 11 illuminating the surface of the sample S; a CCD camera 12 capturing an image of the surface of the sample S; and a turret 16. The turret 16 includes an indenter column 14, which includes the indenter 14a, and a field lens 15. The turret 16 is capable of switching between the indenter column 14 and the field lens 15 by rotating.

The illuminating device 11 shines a light to illuminate the surface of the sample S. The light shone by the illuminating device 11 reaches the surface of the sample S via a lens 1a, a half mirror 1d, a mirror 1e, and the field lens 15.

Based on reflected light input from the surface of the sample S via the field lens 15, the mirror 1e, the half mirror 1d, a mirror 1g, and a lens 1h, the CCD camera 12 obtains image data by capturing an image of the surface of the sample S as well as an indentation formed in the surface of the sample S by the indenter 14a. The CCD camera 12 then outputs the acquired image data to the controller 6 via a frame grabber 17, which is capable of simultaneously accumulating and storing a plurality of frames of image data.

The indenter column 14 is displaced toward the sample S placed on the sample stage 2 by a load mechanism (not shown in the drawings), which is driven in response to a control signal output by the controller 6. The indenter 14a, provided on a forefront end of the indenter column 14, is pressed against the surface of the sample S with a predetermined test force. The present embodiment uses a quadrangular pyramidal Vickers indenter (with opposing angles of 136±0.5°) as the indenter 14a.

The field lens 15 is a collective lens, each lens being configured with a different magnification. A plurality of the field lenses 15 are retained on a bottom surface of the turret 16. The field lens 15 is situated above the sample S by rotating the turret 16. Thereby, the light shone by the illuminating device 11 uniformly illuminates the surface of the sample S.

The turret 16 is configured to enable the indenter column 14 and the plurality of field lenses 15 to be attached to the bottom surface thereof. The turret 16 is also configured to be capable of positioning any one of the indenter column 14 and the plurality of field lenses 15 above the sample S by rotating the turret 16 centered around a Z-axis direction. Specifically, the indentation can be formed in the surface of the sample S by positioning the indenter column 14 above the sample S, and the formed indentation can be observed by positioning the field lenses 15 above the sample S.

The sample S is placed on an upper surface of the sample stage 2 and is fixed in place with a sample holder 2a. The XY stage 3 is driven by a drive mechanism (not shown in the drawings) driven in response to a control signal output by the controller 6. The XY stage 3 then displaces the sample stage 2 in a direction (X and Y directions) perpendicular to a displacement direction (Z direction) of the indenter 14a. The AF stage 4 is driven in response to the control signal output by the controller 6. The AF stage 4 then minutely raises and lowers the sample stage 2 based on the image data captured by the CCD camera 12 to focus on the surface of the sample S. The elevator mechanism 5 is driven in response to the control signal output by the controller 6. The elevator mechanism 5 then changes a relative distance between the sample stage 2 and the field lens 15 by displacing the sample stage 2 (the XY stage 3 and the AF stage 4) in the Z direction. Furthermore, the elevator mechanism 5 can be configured to integrally include the AF stage 4. A configuration is also possible that includes neither the AF stage 4 nor the elevator mechanism 5. In such a case, the hardness measurer 1 may be configured to be movable upward and downward in the Z direction. Specifically, through the upward and downward motion of the hardness measurer 1 in the Z direction, the relative distance between the sample stage 2 and the field lens 15 is changed, enabling achievement of autofocusing which focuses on the surface of the sample S.

The console 7 is configured with a keyboard 71 and a mouse 72. The console 7 receives an operation input by an user during a hardness test. In addition, when the console 7 receives a predetermined input operation performed by the user, a predetermined operation signal corresponding to the input operation is generated and output to the controller 6. Specifically, the console 7 receives an operation in which the user selects a condition determining a focus position of the indentation. The console 7 also receives an operation in which the user designates a range of displacement (a range of relative distance between the sample stage 2 and the field lens 15) of the sample stage 2 (the elevator mechanism 5 and the AF stage 4). In addition, the console 7 receives an operation in which the user inputs a test condition value to be used when carrying out the hardness test with the hardness tester 100. The input test condition value is transmitted to the controller 6. Herein, the test condition value is a value such as a material of the sample S, a test force (N) loaded on the sample S by the indenter 14a, or a magnification power of the field lens 15, for example. In addition, the console 7 receives an operation in which the user selects one of a manual mode, in which the focus position of the indentation is manually determined, and an automatic mode, in which the determination is made automatically. The console 7 also receives an operation in which the user programs a test position to be used when carrying out the hardness test.

The monitor 8 is configured by a display device such as an LCD, for example. The monitor 8 displays, for example, hardness test settings input on the console 7, results of the hardness test, and an image of the surface of the sample S and the indentation formed in the surface of the sample S captured by the CCD camera 12.

Figure 4:
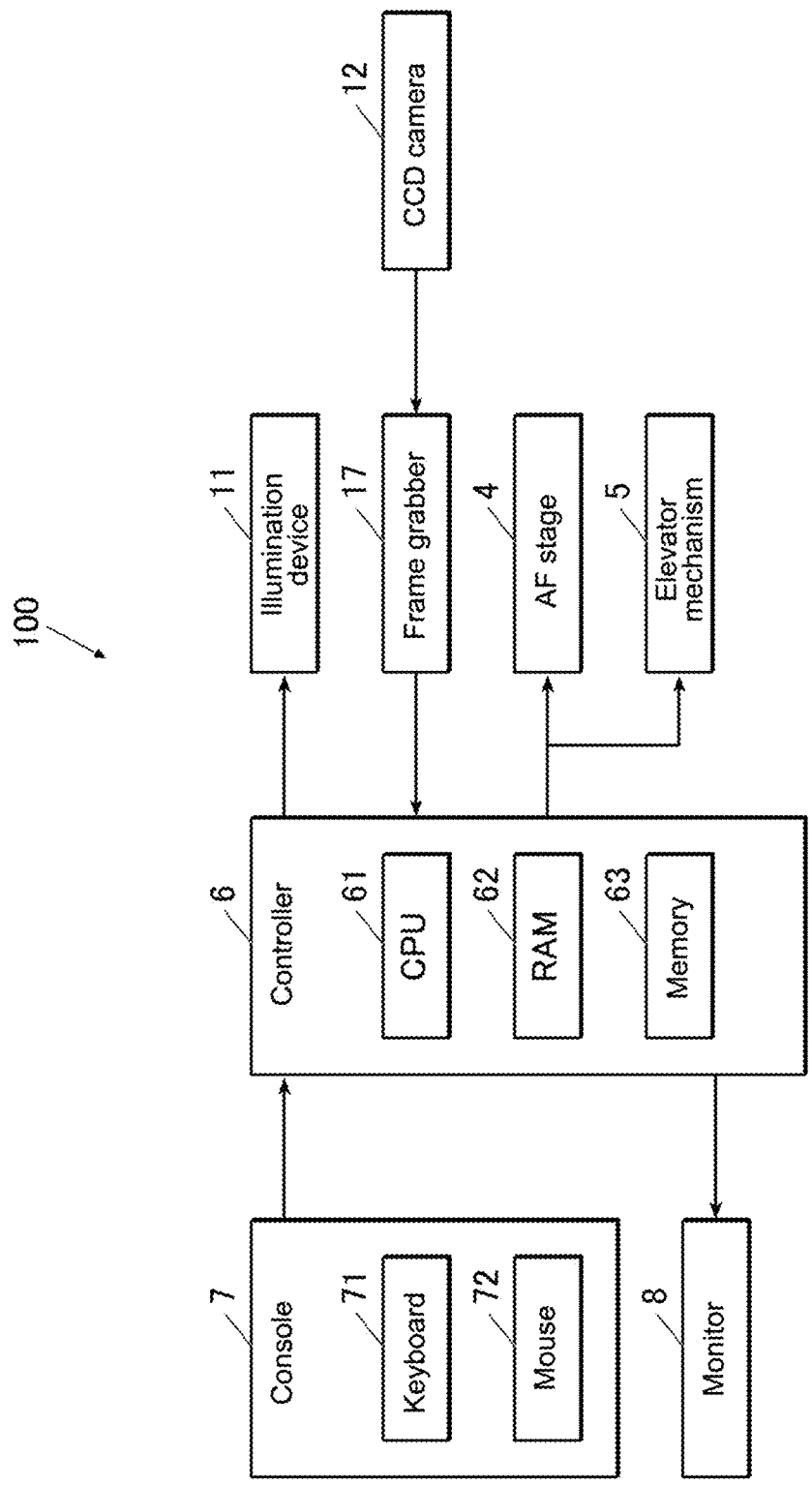
FIG. 4 is a block diagram illustrating a control structure of the hardness tester according to the present invention.

As shown in FIG. 4, the controller 6 is configured to include a CPU 61, a RAM 62, and a memory 63. The controller 6 performs operation control of performance of a predetermined hardness test by executing a predetermined program stored in the memory 63.

The CPU 61 retrieves a processing program stored in the memory 63, then opens and executes the processing program in the RAM 62, thereby performing overall control of the hardness tester 100. The RAM 62 opens the processing program executed by the CPU 61 in a program storage region within the RAM 62 and stores in a data storage region input data, processing results generated during execution of the processing program, and the like. The memory 63 includes, for example, a recording medium (not shown in the drawings) storing a program, data, and the like. The recording medium is configured with a semiconductor memory, for example. In addition, the memory 63 stores various kinds of data, various kinds of processing programs, and data processed by running the programs that allow the CPU 61 to perform overall control of the hardness tester 100. Also, the memory 63 stores a program of a test pattern laid out on one of the samples S (a parts program).

Next, operations of the hardness tester 100 according to the present embodiment are described. First, a process of the user creating and registering the parts program is described. Using the CCD camera 12, the user first captures an image of the shape of a master work piece S0 and acquires an image of the master work piece S0, which is a reference sample to be used as a standard reference when performing repeated measurements of the hardness of samples S having identical shapes. Next, the user defines a coordinate system with respect to the acquired image of the master work piece S0. Then, the user lays out a test pattern with the defined coordinate system as a reference and registers the test pattern as a parts program. Together with a measurement procedure, the parts program logs, in addition to a test position, manually defined measurement conditions such as data on the indenter 14a to be used (placement of the turret 16, shape of the indenter 14a) and the test force. The registered parts program is stored in the memory 63. Thus, the memory 63 is a memory in the present invention. The above completes a parts program registration process.

Next, a process of repeatedly measuring the hardness of samples S having identical shapes in the hardness tester 100 according to the present embodiment is described with reference to a flow chart in FIG. 5. This process is initiated when an instruction operation by the user to initiate automatic testing is detected.

Figure 6:
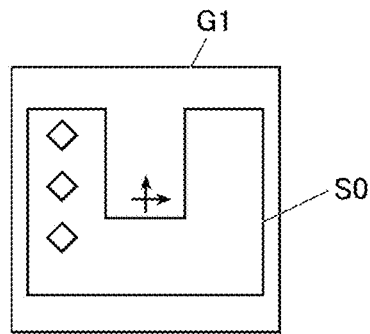
FIG. 6 illustrates an exemplary pattern image.

First, the CPU 61 of the controller 6 executes a "work piece recognition command" in the parts program; performs a pattern searching process with reference to the plurality of samples S to be measured, the CPU 61 performing the pattern searching process using a pattern image G1 (see FIG. 6) based on the image of the master work piece S0; and detects the number of samples S having a shape identical to that of the master work piece S0, as well as the position and angle of each of the samples S having the identical shape (step S101: pattern searching). Specifically, the CPU 61 is a pattern searcher in the present invention.

Next, the CPU 61 defines the number of samples having the identical shape detected in step S101 as "number of repetitions," which is the number of samples S for which the same test pattern is repeated (step S102). Specifically, the CPU 61 is a sample count definer in the present invention.

Figure 7:
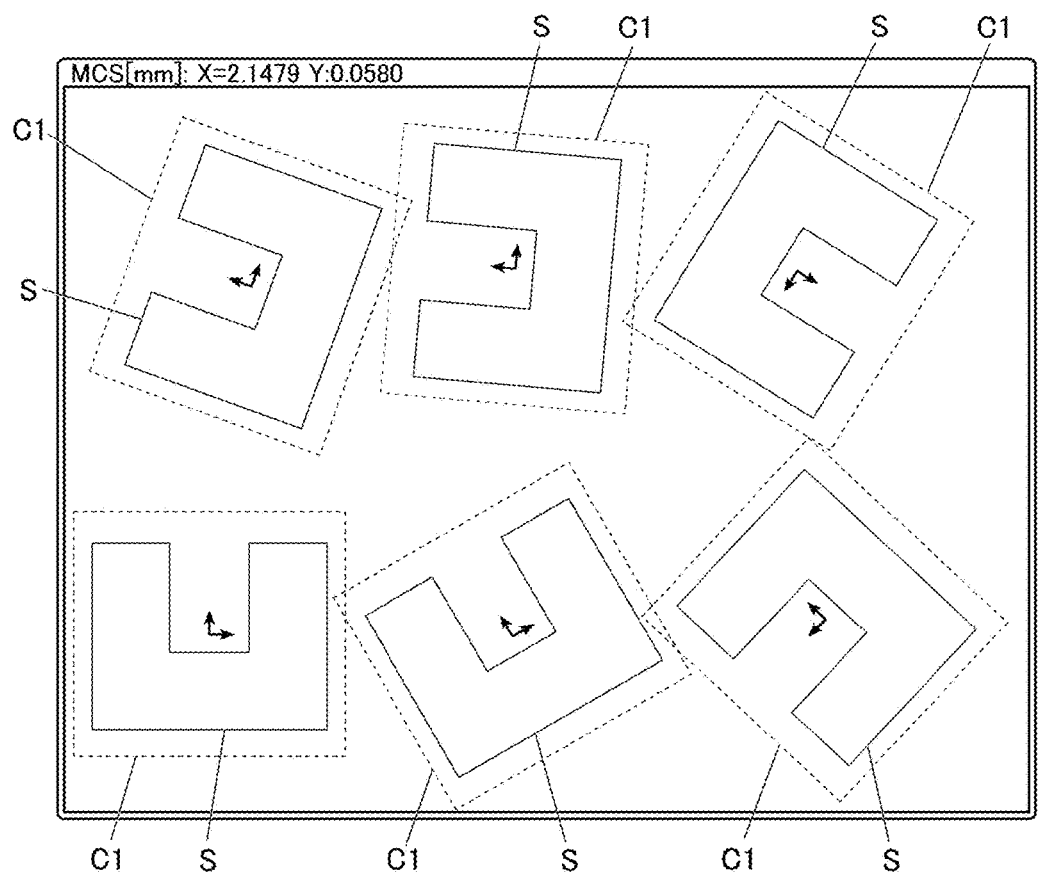
FIG. 7 illustrates an exemplary format where a coordinate system is defined for each of the samples.

Next, the CPU 61 executes a "work piece offset command" in the parts program; generates coordinate system data with respect to each of the samples S based on: the position and angle of each of the samples S having the identical shape detected in step S101, and the parts program stored in the memory 63; and then defines a coordinate system and test pattern (test position) for the sample S to be measured (step S103: pattern definition). Specifically, the CPU 61 is a pattern definer in the present invention. FIG. 7 illustrates an exemplary format where a coordinate system C1 is defined for each of the samples S.

Next, the CPU 61 executes hardness testing (pattern testing) with respect to the sample S for which the coordinate system and test position have been defined in step S103; and measures the hardness of the sample S (step S104: measurement). The hardness testing is, more specifically, a process measuring the hardness of the sample S by loading a predetermined test force with the indenter 14a to form an indentation in each test position on the surface of the sample S, then measuring dimensions of the indentations. Specifically, the CPU 61 is a measurer in the present invention.

Next, the CPU 61 determines whether measurement has been performed for the number of repetitions defined in step S102 (step 5105). In a case where the CPU 61 determines that measurement has been performed for the number of repetitions (step S105: YES), the CPU 61 determines that all of the measurements have been performed and the process ends. Meanwhile, in a case where the CPU 61 determines that measurement has not been performed for the number of repetitions (step S105: NO), the CPU 61 determines that measurement of at least one sample S has not been performed, moves to step S103, and then defines the coordinate system and test position for the sample S to be measured. Through the above-noted process, repeated measurement of the hardness of the samples S having identical shapes can be performed.

As noted above, the hardness tester 100 according to the present embodiment includes: the memory (memory 63) storing, as a parts program, definitions of measurement conditions including a coordinate system and test position, which are defined with respect to an image of the standard reference sample (master work piece S0), which is a reference sample to be used as a standard reference when performing repeated measurements of the hardness of samples S having identical shapes; the pattern searcher (CPU 61) performing a pattern searching process with reference to the plurality of samples S to be measured, the pattern searcher performing the pattern searching process using a pattern image based on the image of the standard reference sample, and detecting the number of samples having a shape identical to that of the standard reference sample, as well as the position and angle of each of the samples having the identical shape; the pattern definer (CPU 61) defining a coordinate system and test position for each of the samples S having the identical shape, based on the position and angle of each of the samples S having the identical shape detected by the pattern searcher; and the measurer (CPU 61) executing hardness testing with respect to the samples S for which the coordinate system and test position have been defined by the pattern definer, and measuring the hardness of the samples S. Accordingly, with the hardness tester 100 of the present embodiment, when repeatedly measuring the hardness of a plurality of samples S having identical shapes, the measurement can be performed automatically irrespective of the number and orientations (postures) of the samples S. This obviates the need for the user to perform a recovery task or an operation to omit the measurement, and can improve operability. In addition, jigs arranging the plurality of samples S in an array are unnecessary and costs can therefore be reduced.

In addition, according to the hardness tester 100 of the present embodiment, after the hardness of one sample S is measured by the measurer, the pattern definer defines the coordinate system and test position for the next sample S to be measured from among the samples S having the identical shape. Accordingly, with the hardness tester 100 of the present embodiment, by successively defining the coordinate system and test position for the sample S to be measured, a task of defining the coordinate system and test position is performed as needed. Therefore, in cases where an error occurs and the user wishes to end the measurement partway through, for example, the task of defining the coordinate system and test position for the unmeasured samples S can be omitted and measurement can be conducted efficiently with no waste.

In addition, the hardness tester 100 according to the present embodiment includes a sample count definer (CPU 61), which defines the number of samples having the identical shape detected by the pattern searcher as a number of repetitions, which is the number of samples S for which the same test pattern is repeated. Therefore, with the hardness tester 100 according to the present embodiment, an operation by the user to define the number of repetitions can be omitted, and therefore operability can be further improved and a measurement task can be made more efficient and the time involved in the measurement task can be reduced.

In the above, a concrete description is given based on an embodiment according to the present invention. However, the present invention is not limited to the above-described embodiment and can be modified without deviating from the scope of the invention.

Modifications

Figure 8:
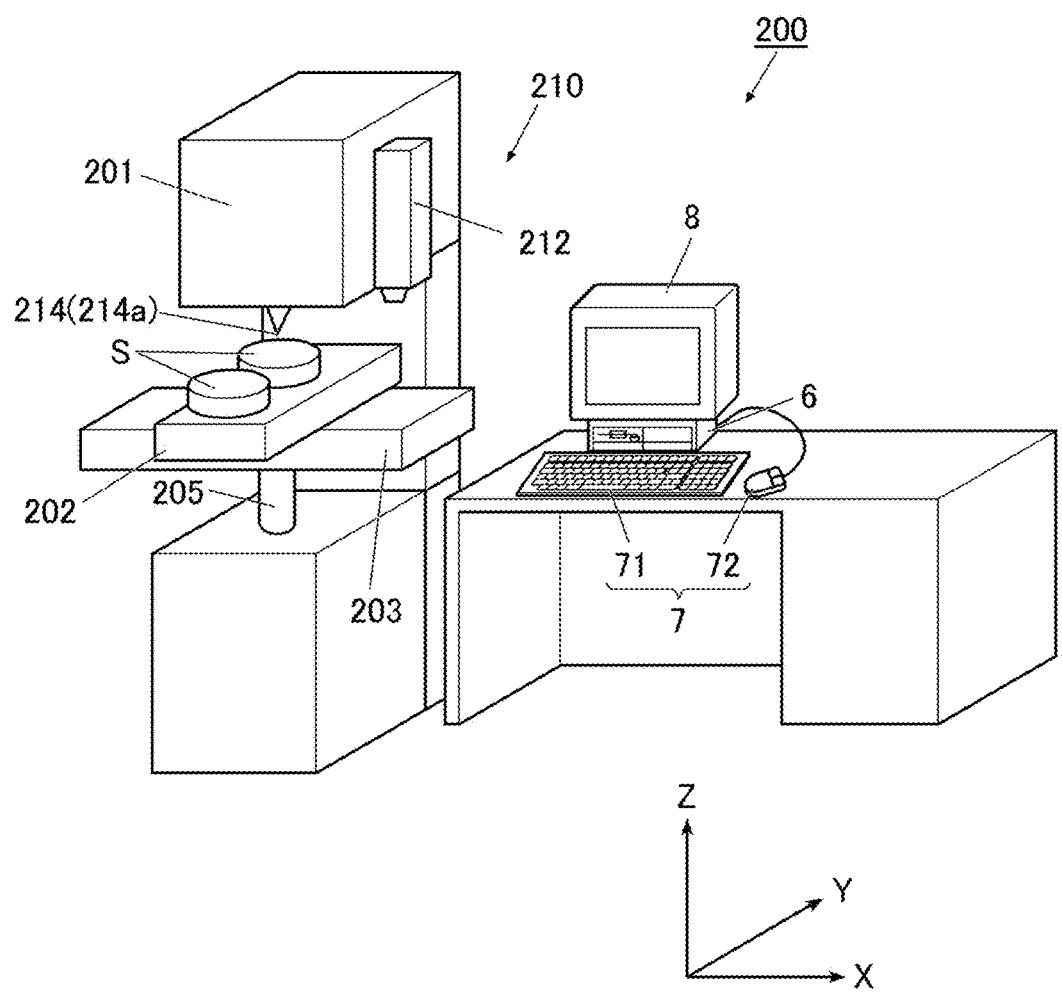
FIG. 8 is a perspective view illustrating an overall configuration of a hardness tester according to a modification.
Figure 9:
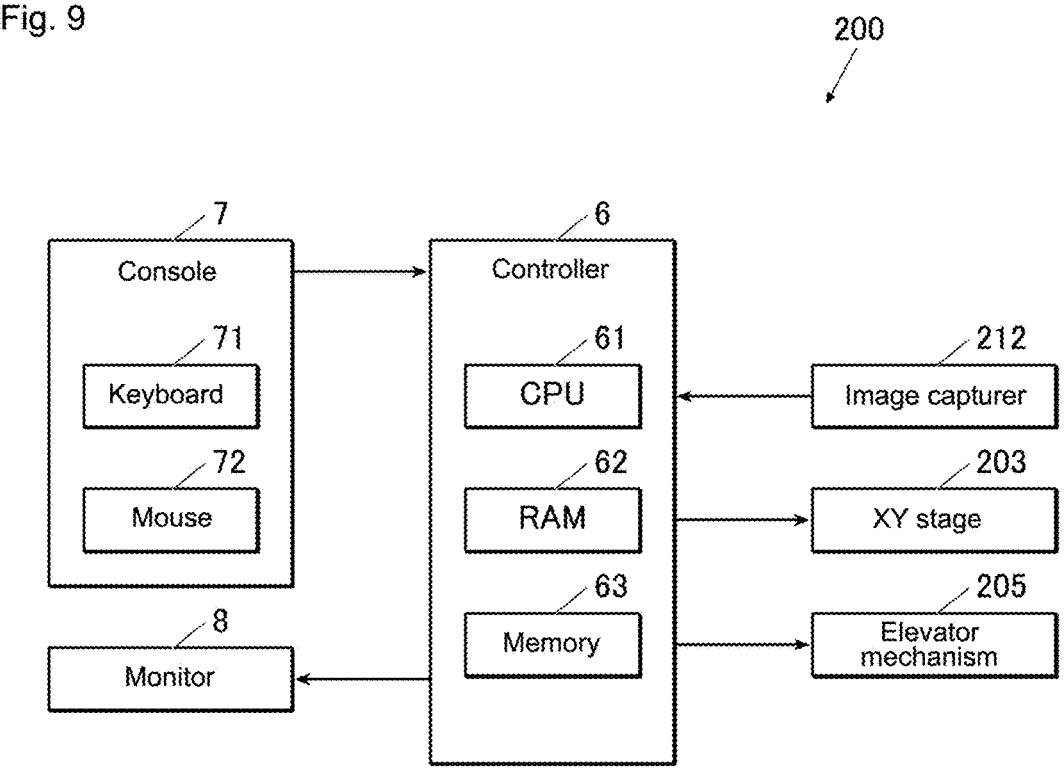
FIG. 9 is a block, diagram illustrating a control structure the hardness tester according to the modification.
Figure 10:
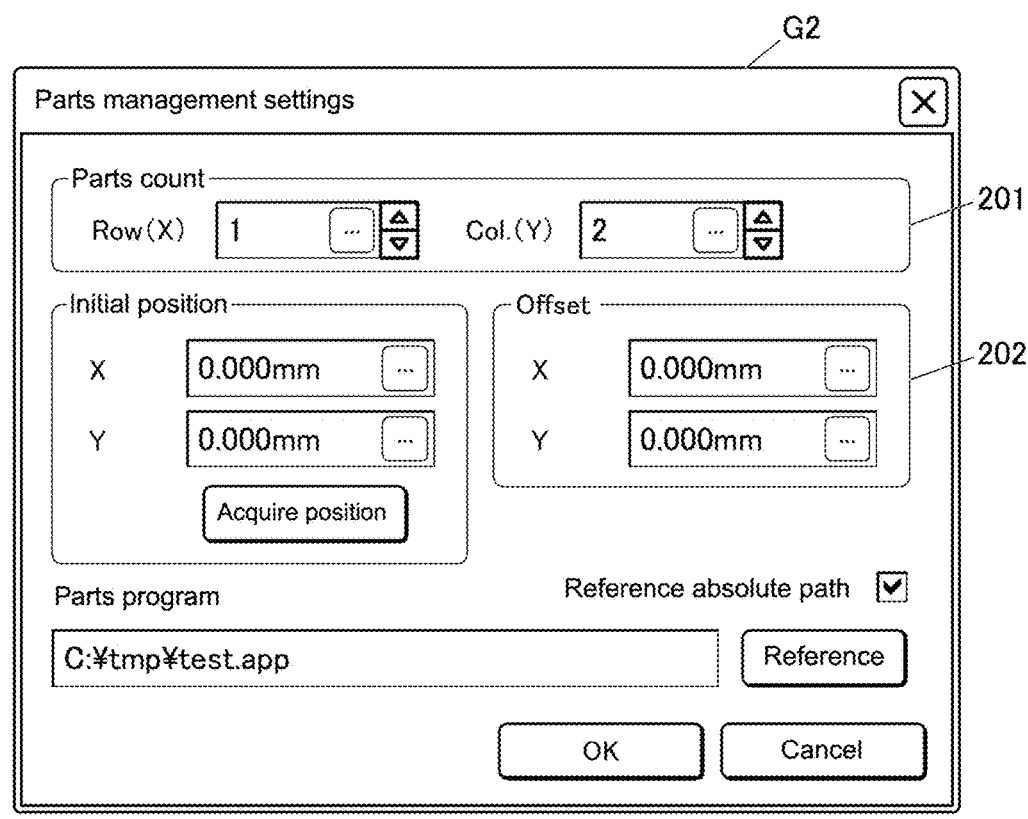
FIG. 10 illustrates an exemplary parts manager settings screen.
Figure 11:
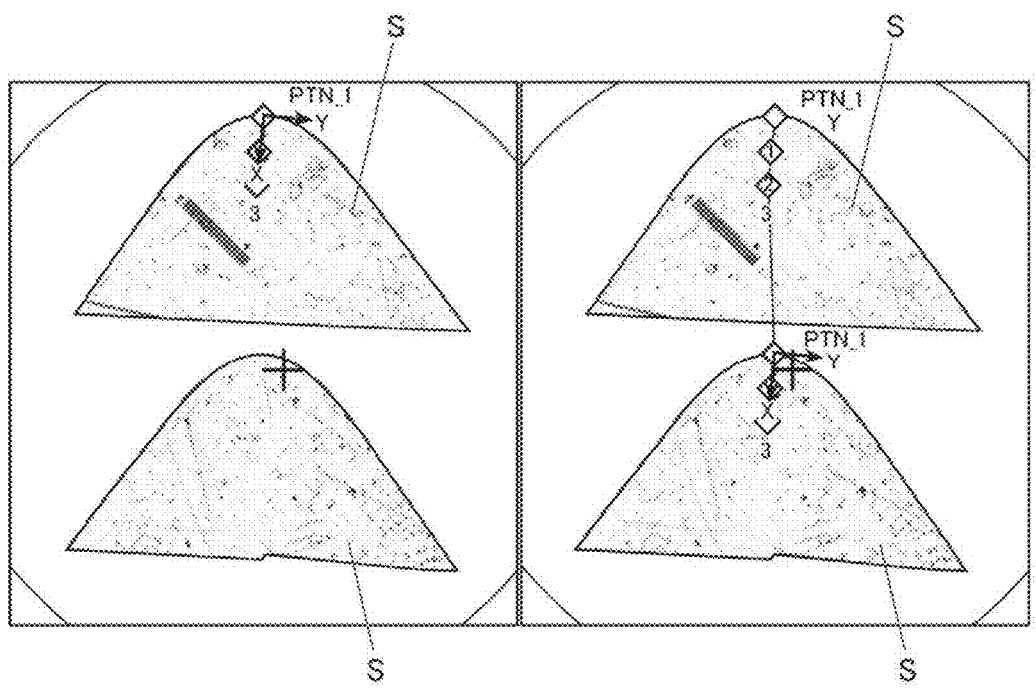
FIG. 11 illustrates an exemplary format where an orientation and interval of a plurality of samples have an orderly arrangement.

In addition, in the above-described embodiment, a Vickers hardness tester is described to exemplify the hardness tester 100. However, the present invention is not limited to this. For example, FIGS. 8 and 9 show a Rockwell hardness tester 200 as a modification. Moreover, in order to simplify the description, identical reference numerals are assigned to configurations similar to those in the embodiment and a detailed description thereof is omitted.

As shown in FIGS. 8 to 9, the hardness tester 200 is configured to include a tester main body 210, the controller 6, the console 7, and the monitor 8.

As shown in FIG. 8, the tester main body 210 includes a hardness measurer 201 measuring hardness of the samples S; a sample stage 202 on which the samples S are placed; an XY stage 203 displacing the sample stage 202; and an elevator mechanism 205 raising and lowering the sample stage 202 (the XY stage 203).

The hardness measurer 201 is configured to include an image capturer 212 capturing an image of the surface of the sample S, and an indenter column 214 provided with an indenter 214*a*.

The image capturer 212 is arranged at a position offset from the indenter column 214 in the left-right direction (X direction). The amount of offset between a center of the indenter column 214 and a center of the image capturer 212 is determined in advance. The image capturer 212 is configured to include, for example: an illumination device illuminating the surface of the sample S; a CCD camera capturing an image of the surface of the sample S and acquiring image data; a field lens arranged on a bottom surface of the image capturer 212 and through which light reflected by the surface of the sample S passes; and an optical system. guiding the light passing through the field lens to the CCD camera. The image capturer 212 outputs the acquired image data of the surface of the sample S to the controller 6.

The indenter column 214 is displaced toward the sample S placed on the sample stage 202 by a load mechanism (not shown in the drawings), which is driven in response to a control signal output by the controller 6. The indenter 214*a*, provided on a forefront end of the indenter column 214, is pressed against the surface of the sample S with a predetermined test force. In a modification, a Rockwell diamond conical indenter having a point angle of 120° or ball indenter (for example, an indenter having a diameter of $\frac{1}{16}$ inch, $\frac{1}{8}$ inch, $\frac{1}{4}$ inch, or $\frac{1}{2}$ inch) is used.

The sample S is placed on an upper surface of the sample stage 202. The XY stage 203 is driven by a drive mechanism (not shown in the drawings) driven in response to a control signal output by the controller 6. The XY stage 203 then displaces the sample stage 202 in a direction (X and Y directions) perpendicular to a displacement direction (Z direction) of the indenter 214a. The XY stage 203 has a stroke which takes into consideration an amount of offset between the center of the indenter column 214 and the center of the image capturer 212. The elevator mechanism 205 is driven in response to the control signal output by the controller 6. The elevator mechanism 205 then changes a relative distance between the sample stage 202 and the field lens of the image capturer 212 by displacing the sample stage 202 (the XV stage 203) in the Z direction. Moreover, the configuration may include an AF stage which enables focusing on the surface of the sample S by minutely raising and lowering the sample stage 202 based on the image data captured by the image capturer 212. Furthermore, the elevator mechanism 205 can be configured to integrally include the AF stage. A configuration is also possible that does not include the elevator mechanism 205. In such a case, the hardness measurer 201 may be configured to be movable upward and downward in the Z direction. Specifically, through the upward and downward motion of the hardness measurer 201 in the Z direction, the relative distance between the sample stage 202 and the field lens of the image capturer 212 is changed, enabling achievement of autofocusing which focuses on the surface of the sample S.

The hardness tester 200 according to the modification performs a measurement by first applying an initial test force to the surface of the sample S with the indenter 214a, then applying a true test force which adds an additional test force to the initial test force, then once more reverting to the initial test force. The hardness tester 200 measures the hardness of the sample S based on a difference in pressing depth of the indenter 214a during the first and second applications of the initial test force (Rockwell hardness test).

The hardness tester 200 according to the modification recognizes the shape of the sample S by acquiring image data of the surface of the sample S with the image capturer 212. When the image capturer 212 acquires the image data, the XY stage 203 is offset rightward in the X direction from the center of the indenter column 214. The CPU 61 of the hardness tester 200 automatically opens the test pattern based on the recognized shape of the sample S. When executing the hardness test (pattern test), the CPU 61 executes the test by restoring the offset of the XY stage 203 to its original state.

In addition, in the hardness tester 200 according to the modification, a task of arranging the test pattern (parts program registration process), for example, is performed using the console 7 and monitor 8, as in the embodiment. Also, because the hardness tester 200 according to the modification performs a process similar to that of the embodiment shown in FIG. 5, a description of the process of repeatedly measuring the hardness of the samples S having the identical shape is omitted.

As noted above, with the hardness tester 200 (Rockwell hardness tester) according to the modification, when repeatedly measuring the hardness of the plurality of samples S having identical shapes, the measurement can be performed automatically irrespective of the number and orientations (postures) of the samples S. Accordingly, effects similar to those of the hardness tester 100 (Vickers hardness tester) according to the embodiment can be obtained.

Additional Modifications

Figure 5:
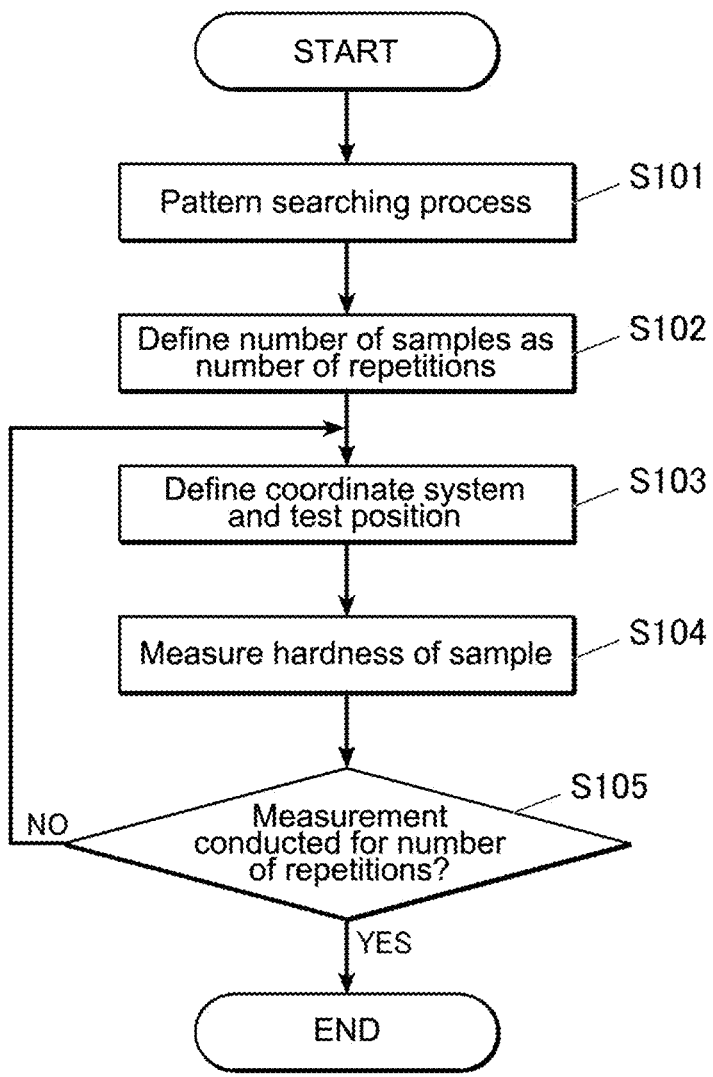
FIG. 5 is a flow chart illustrating a process of the hardness tester according to the present invention, in which hardness of samples having an identical shape is repeatedly measured.

In addition, in the above-described embodiment, in step S103 of FIG. 5, the coordinate system and test position are defined for the next sample S to be measured from among the samples S having the identical shape. However, the present invention is not limited to this. For example, the coordinate system and test position may be defined for all of the samples S having the identical shape, rather than only for the next sample S to be measured.

In addition, in the above-described embodiment, in step S102 of FIG. 5, the number of samples having the identical shape detected in step S101 is defined as the number of repetitions, which is the number of samples S for which the same test pattern is repeated. However, the present invention is not limited to this. For example, the number of samples having an identical shape detected in step S101 may be displayed on the monitor 8, and the user checking the display content may compare the display content with the actual number of samples, after which the user may manually define the number of repetitions. Accordingly, even in a case where the actual number of samples differs from the detected number of samples, for example, the correct number of repetitions can be defined, and therefore measurement errors can be more reliably avoided.

In addition, in the above-described embodiment, in step S104 of FIG. 5, hardness testing is performed for each of the samples S. However, the present invention is not limited to this. For example, in a state where the test position is defined ahead of time for all of the samples S having the identical shape, the shortest test route when executing a single hardness test for all of the samples S having the identical shape can be calculated based on the defined test position. In this case, the CPU 61 is a calculator in the present invention. Accordingly, an amount of time spent in performing hardness testing can be minimized, and thus a measurement task can be performed with even greater efficiency.

In addition, in the above-described embodiment, in step S101 of FIG. 5, when the pattern searching process is performed, the pattern image based on the overall image of the master work piece S0 is used. However, the present invention is not limited to this. For example, a configuration is possible in which only a characteristic portion is extracted from the shape of the master work piece S0 and the pattern searching process is performed using a pattern image based on an image of the extracted characteristic portion. For example, in a case where the master work piece S0 has a toothed gear shape, a configuration is possible in which only a portion having one or a plurality of teeth is extracted and the pattern searching process is performed using a pattern image based on an image of the one or plurality of teeth.

in addition, in the above-described embodiment, a Vickers hardness tester is described to exemplify the hardness tester 100. However, the present invention is not limited to this. The present invention may be applied to any hardness tester having an indenter with a known shape. For example, the present invention may also be applied to a Knoop hardness tester having a quadrangular pyramid diamond indenter.

In addition, within a scope not deviating from the substance of the present invention, appropriate modifications may also be made to detailed structures and operations of each component configuring the hardness tester 100.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects.

Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester for measuring hardness of a sample by loading a predetermined test force on the sample with an indenter to form an indentation in a surface of the sample, then performing one of a measurement of dimensions of the indentation and a measurement of a pressing depth of the indenter when forming the indentation, the hardness tester comprising:
 a memory configured to store, as a parts program, definitions of measurement conditions including a coordinate system and test position, which are defined with respect to an image of a standard reference sample to be used as a standard reference when performing repeated measurements of the hardness of samples having identical shapes; and
 a processor configured to execute the parts program stored in the memory and causing the processor to perform operations, comprising:
  pattern searching, with reference to a plurality of samples to be measured, using a pattern image based on the image of the standard reference sample, and detecting a number of samples, from the plurality of samples to be measured, having a shape identical to that of the standard reference sample, as well as a position and angle of each of the samples having the identical shape;
  defining a coordinate system and test position for each of the samples having the identical shape, based on the position and angle of each of the samples having the identical shape detected by the pattern searching, and on the parts program stored in the memory;
  calculating the shortest test route when executing a single hardness test for all of the samples having the identical shape, based on the test position defined by the defining for each sample having the identical shape; and
  executing hardness testing based on the calculated test route with respect to the samples for which the coordinate system and test position have been defined by the defining, and measuring the hardness of the samples.

2. The hardness tester according to claim 1, wherein after the hardness of one sample is measured, the defining defines the coordinate system and test position for the next sample to be measured from among the samples having the identical shape.

3. The hardness tester according to claim 1, wherein the operations further comprise defining the number of samples having the identical shape detected by the pattern searching as a number of repetitions, which is the number of samples for which the same test pattern is repeated.

4. The hardness tester according to claim 2, wherein the operations further comprise defining the number of samples having the identical shape detected by the pattern searching as a number of repetitions, which is the number of samples for which the same test pattern is repeated.

5. A hardness testing method of a hardness tester measuring hardness of a sample by loading a predetermined test force on the sample with an indenter to form an indentation in a surface of the sample, then performing one of a measurement of dimensions of the indentation and a measurement of a pressing depth of the indenter when forming the indentation, the hardness testing method comprising:
 performing a pattern searching process with reference to a plurality of samples to be measured, the pattern searching process being performed using a pattern image based on an image of a standard reference sample to be used as a standard reference when performing repeated measurements of the hardness of samples having identical shapes, and detecting a number of samples, from the plurality of samples to be measured, having a shape identical to that of the standard reference sample, as well as a position and angle of each of the samples having the identical shape;
 defining a coordinate system and test position for each of the samples having the identical shape based on the position and angle of each of the samples having the identical shape detected in the pattern searching, and on a parts program defining measurement conditions, including a coordinate system and test position, with respect to an image of the standard reference sample;
 calculating the shortest test route when executing a single hardness test for all of the samples having the identical shape, based on the test position defined by the defining for each sample having the identical shape; and
 measuring the hardness of the samples, based on the calculated test route, for which the coordinate system and test position have been defined in the defining of the coordinate system and the test position.

6. The method according to claim 5, further comprising defining, after the hardness of one sample is measured, the coordinate system and test position for the next sample to be measured from among the samples having the identical shape.

7. The hardness tester according to claim 5, further comprising defining the number of samples having the identical shape detected by the pattern searching as a number of repetitions, which is the number of samples for which the same test pattern is repeated.

8. The hardness tester according to claim 6, further comprising defining the number of samples having the identical shape detected by the pattern searching as a number of repetitions, which is the number of samples for which the same test pattern is repeated.

* * * * *